United States Patent
Rusek

(10) Patent No.: US 8,907,150 B2
(45) Date of Patent: Dec. 9, 2014

(54) BIOGENIC FUEL AND METHOD OF MAKING SAME

(75) Inventor: John J. Rusek, West Lafayette, IN (US)

(73) Assignee: Swift Fuels, LLC, West Lafayette, IN (US)

( * ) Notice: Subject to any disclaimer, the term of this patent is extended or adjusted under 35 U.S.C. 154(b) by 643 days.

(21) Appl. No.: 13/217,411

(22) Filed: Aug. 25, 2011

(65) Prior Publication Data

US 2012/0059205 A1    Mar. 8, 2012

Related U.S. Application Data

(63) Continuation-in-part of application No. 13/028,896, filed on Feb. 16, 2011, now Pat. No. 8,552,232, which (Continued)

(51) Int. Cl.
*C10L 1/16* (2006.01)
*C10L 1/10* (2006.01)

(Continued)

(52) U.S. Cl.
CPC .. *C10L 1/02* (2013.01); *B01J 37/03* (2013.01); *C10L 1/023* (2013.01); *C10G 3/50* (2013.01); *C10G 2400/04* (2013.01); *Y02T 50/678* (2013.01); *C07C 1/2074* (2013.01); *C07C 4/10* (2013.01); *C12P 7/16* (2013.01); *B01J 23/20* (2013.01); *Y02E 50/10* (2013.01); *C10L 1/1824* (2013.01); *C10L 1/1608* (2013.01); *C07C 2523/20* (2013.01); *C07C 5/08* (2013.01); *C10L 1/04* (2013.01); *C10G 2300/4018* (2013.01); *B01J 21/08* (2013.01); *C12P 2203/00* (2013.01); *C10G 3/44* (2013.01);

(Continued)

(58) Field of Classification Search
USPC ........... 502/353, 240, 246, 247; 585/302, 585/240–242
See application file for complete search history.

(56) References Cited

U.S. PATENT DOCUMENTS

| 1,315,585 A | 9/1919 | Weizmann |
| 1,713,589 A | 5/1929 | Bereslavsky |

(Continued)

FOREIGN PATENT DOCUMENTS

| EP | 0460957 | 12/1991 |
| EP | 0526129 | 2/1993 |

(Continued)

OTHER PUBLICATIONS

International Search Report and Written Opinion issued in PCT/US2012/050884, dated Feb. 26, 2013.

(Continued)

*Primary Examiner* — Pamela H Weiss
(74) *Attorney, Agent, or Firm* — Woodard, Emhardt, Moriarty, McNett & Henry LLP

(57) ABSTRACT

A method of producing from a biomass mesitylene-isopentane fuel is provided. A biomass may be fermented to form acetone. The acetone is converted in a catalytic reactor to mesitylene and mesityl oxide. The mesitylene is separated in a phase separator and the organic face containing mesityl oxide is sent to a dehydration reactor, then to a demethylation reactor, and finally to a hydrogenation reactor from which isopentane is recovered. This isopentane is then mixed with the mesitylene to form the final mesitylene-isopentane fuel. The catalytic reaction with acetone employs catalysts of either niobium, vanadium or tantalum.

35 Claims, 11 Drawing Sheets

Related U.S. Application Data is a continuation-in-part of application No. 12/788,010, filed on May 26, 2010, now Pat. No. 8,344,193, which is a continuation-in-part of application No. 12/717,480, filed on Mar. 4, 2010, now Pat. No. 8,556,999, which is a continuation-in-part of application No. 12/139,428, filed on Jun. 13, 2008, now Pat. No. 8,049,048, which is a continuation-in-part of application No. 11/881,565, filed on Jul. 27, 2007, now abandoned.

(60) Provisional application No. 60/833,589, filed on Jul. 27, 2006.

(51) Int. Cl.

| | | |
|---|---|---|
| *C10L 1/04* | (2006.01) | |
| *C07C 7/20* | (2006.01) | |
| *B01J 37/03* | (2006.01) | |
| *C10L 1/02* | (2006.01) | |
| *C10G 3/00* | (2006.01) | |
| *C07C 1/207* | (2006.01) | |
| *C07C 4/10* | (2006.01) | |
| *C12P 7/16* | (2006.01) | |
| *B01J 23/20* | (2006.01) | |
| *C07C 5/08* | (2006.01) | |
| *C10G 45/32* | (2006.01) | |
| *C10L 1/08* | (2006.01) | |
| *C12P 7/36* | (2006.01) | |
| *C07C 5/03* | (2006.01) | |
| *C10L 1/182* | (2006.01) | |
| *B01J 21/08* | (2006.01) | |

(52) U.S. Cl.
CPC . *C10G 45/32* (2013.01); *C10L 1/08* (2013.01); *C10G 2300/1014* (2013.01); *C12P 7/36* (2013.01); *C07C 5/03* (2013.01); *Y02E 50/343* (2013.01); *C10G 2300/1018* (2013.01); *C10G 2400/02* (2013.01); *C10G 2400/08* (2013.01); *C10G 2300/4012* (2013.01); *Y02E 50/13* (2013.01); *C10G 2300/4006* (2013.01); *C07C 2523/22* (2013.01)
USPC ........... 585/242; 585/240; 585/241; 585/302; 502/240; 502/246; 502/247; 502/353

(56) References Cited

U.S. PATENT DOCUMENTS

| | | | |
|---|---|---|---|
| 2,401,983 A | 6/1946 | Stanly et al. | |
| 2,413,262 A | 12/1946 | Stirton | |
| 2,422,674 A | 6/1947 | Haensel et al. | |
| 2,425,096 A | 8/1947 | Ipatieff et al. | |
| 2,425,559 A | 8/1947 | Passino et al. | |
| 2,506,539 A | 5/1950 | Boardman | |
| 2,589,621 A | 3/1952 | McCaulay et al. | |
| 2,593,561 A | 4/1952 | Herbst et al. | |
| 2,917,561 A | 12/1959 | Eby | |
| 3,201,485 A | 8/1965 | Kovach | |
| 3,267,165 A | 8/1966 | Kimble et al. | |
| 3,301,912 A | 1/1967 | Hwang et al. | |
| 3,946,079 A | 3/1976 | Mizutani et al. | |
| 4,006,149 A | 2/1977 | Bonnemann et al. | |
| 4,300,009 A | 11/1981 | Haag et al. | |
| 4,368,056 A | 1/1983 | Pierce et al. | |
| 4,398,920 A | 8/1983 | Guibet et al. | |
| 4,398,921 A | 8/1983 | Rifkin et al. | |
| 4,535,187 A | 8/1985 | Papa et al. | |
| 5,063,156 A | 11/1991 | Glassner et al. | |
| 5,087,781 A * | 2/1992 | Schutz et al. | ................. 585/409 |
| 6,271,433 B1 | 8/2001 | Keady et al. | |
| 6,353,143 B1 | 3/2002 | Fang et al. | |
| 6,555,350 B2 | 4/2003 | Ahring et al. | |
| 6,648,931 B1 | 11/2003 | Rao | |
| 6,908,591 B2 | 6/2005 | MacPhee et al. | |
| 6,982,155 B1 | 1/2006 | Fukuda et al. | |
| 6,991,810 B1 | 1/2006 | Grundy et al. | |
| 6,998,050 B2 | 2/2006 | Nakajoh et al. | |
| 7,141,083 B2 | 11/2006 | Jordan | |
| 7,462,207 B2 | 12/2008 | Clark | |
| 7,834,230 B2 | 11/2010 | Fujimoto et al. | |
| 8,556,999 B2 * | 10/2013 | Rusek et al. | .................... 44/307 |
| 2002/0055663 A1 | 5/2002 | Barnes et al. | |
| 2003/0183554 A1 | 10/2003 | Bazzani et al. | |
| 2004/0020106 A1 | 2/2004 | Tack et al. | |
| 2004/0225170 A1 | 11/2004 | Dalloro et al. | |
| 2006/0051848 A1 | 3/2006 | Nishio et al. | |
| 2007/0135318 A1 | 6/2007 | Singh et al. | |
| 2007/0175088 A1 | 8/2007 | Selkirk | |
| 2008/0168706 A1 | 7/2008 | Rusek et al. | |
| 2008/0244961 A1 | 10/2008 | Rusek et al. | |
| 2008/0244962 A1 | 10/2008 | Abhari et al. | |
| 2009/0000185 A1 | 1/2009 | Aulich et al. | |
| 2009/0013591 A1 | 1/2009 | Braden et al. | |
| 2009/0117619 A1 | 5/2009 | Hutcheson et al. | |
| 2009/0203098 A1 | 8/2009 | Verser | |
| 2010/0268005 A1 | 10/2010 | Rusek et al. | |
| 2010/0298615 A1 | 11/2010 | Rusek et al. | |

FOREIGN PATENT DOCUMENTS

| | | |
|---|---|---|
| JP | 57145181 | 9/1982 |
| JP | 62-278989 | 12/1987 |
| WO | WO 98/51813 | 11/1998 |
| WO | WO 2008/013922 A1 | 1/2008 |
| WO | WO 2009/152495 A2 | 12/2009 |

OTHER PUBLICATIONS

Bird, C.W., Transition Metal Intermediates in Organic Syntehsis, New York, Lond: Academic Press, 1967, pp. 1-29.

Colket et al., Development of an Experimental Database and Kinetic Models for Surrogate Jet Fuels, Mar. 1, 2007, American Institute of Aeronautics, pp. 1-21.

International Search Report and Written Opinion issued on Oct. 19, 2011, in corresponding International Application No. PCT/US2011/037505.

International Search Report issued on Nov. 8, 2011 in corresponding International Application No. PCT/US2011/026948.

Roubaud et al, Oxidation and Combustion of Low Alkylbenzenes at High Pressure, 2000, Combustion and Flame 121:535-541.

Zaldivar et al. Abstract, Applied Microbiology Biotechnology (2001), pp. 17-34, vol. 56.

* cited by examiner

BIOGENIC FUEL AND METHOD OF MAKING SAME

REFERENCE TO RELATED APPLICATIONS

This is a continuation-in-part of U.S. patent application Ser. No. 13/028,896, filed Feb. 16, 2011, now U.S. Pat. No. 8,552,232, which is a continuation-in-part of U.S. patent application Ser. No. 12/788,010, filed May 26, 2010, now U.S. Pat. No. 8,344,193, which is a continuation-in-part of U.S. patent application Ser. No. 12/717,480, filed Mar. 4, 2010, now U.S. Pat. No. 8,556,999, which is a continuation-in-part of U.S. patent application Ser. No. 12/139,428, filed Aug. 13, 2008, now U.S. Pat. No. 8,049,048, which is a continuation-in-part of U.S. patent application Ser. No. 11/881,565, filed Jul. 27, 2007, now abandoned, which claims priority of provisional U.S. Patent Application Ser. No. 60/833,589, filed Jul. 27, 2006, the contents of all of which are incorporated herein by reference.

FIELD OF THE INVENTION

The present invention relates in general to an engine fuel produced from renewable materials and, in particular, the present invention provides a non-petroleum based fuel comprised of mesitylene and isopentane which can be produced fully from renewable materials. Further, a method of production for same involving a novel catalyst is provided for producing this fuel.

BACKGROUND OF THE INVENTION

With the end of cheap oil and the mounting peak of world oil production, it is recognized that petroleum is a non-renewable resource and will eventually be depleted. This realization has sparked a renewed interest in the development of renewable sources for fuel. This is particularly true in the case of aviation fuels.

In the United States, the Federal Aviation Administration (FAA) is responsible for setting the technical standards for aviation fuels through (ASTM) International. Any new fuel must comply with an existing fuel specification. For example, the FAA uses as a standard for aviation gasoline ASTM D910-Grade 100LL. This is true whether the new fuel is based on petroleum or a chemical or chemical combination.

Ethanol-based fuels for internal combustion engines have been available for roughly five decades. The State of California originated mandatory oxygenation of motor fuels, which includes ethanol-based fuels, partly to decrease the wholesale cost of fuel, and to a lesser extent to reduce air pollution per gallon of gasoline consumed. Effectively, since ethanol-based fuels have lower energy, pollution is generally increased per mile. A key benefit of ethanol-based fuels is that they have a slightly higher octane number than ethanol-free gasoline. This is the reason many oil companies provide high ethanol containing premium fuels and lower ethanol regular grades of gasoline. Renewable fuels made from some chemical species other than ethanol have been found to exhibit significantly higher octane numbers and increased energy per unit volume when compared to commercial fuels and ethanol-based fuels.

Octane (Power)

Octane number is a measure of the effectiveness of power production. It is a kinetic parameter, therefore difficult to predict. The American Society for Testing and Materials compiled volumes of experimental octane data (for pure hydrocarbons) for the Department of Defense in the 1950's. The method used to obtain this dynamic parameter is discussed in the next paragraph. 2,2,4-trimethyl pentane (isooctane) has a defined octane number of 100, and n-heptane has a defined octane number of 0, based on experimental tests. Octane numbers are linearly interpolated by this method; hence predictions for mixes can be made once pure sample values are determined.

Automobile gasoline is placarded at the pump as the average of Research and Motor octane numbers. These correlate to running a laboratory test engine (CFR) under less severe and more severe conditions, respectively. Effective octane numbers lie between the Research and Motor octane values. Aviation gasoline has a "hard" requirement of 100 MON (motor octane number); ethanol has a MON of 96, which makes its use only viable when mixed with other higher octane components. Conventional 100LL (i.e., 100 octane low lead) contains a maximum of 3 ml of tetraethyl lead per gallon to achieve the desired octane rating.

Range (Energy)

The inherent energy contained within gasoline is directly related to mileage, not to octane number. Automobile gasoline has no energy specification, hence no mileage specification. In contrast, aviation fuels, a common example being 100 LL (100 octane low lead), have an energy content specification. This translates to aircraft range and to specific fuel consumption. In the octane examples above, i-octane and n-heptane had values of 100 and 0, respectively. From an energy perspective, they contain heat of combustion values of 7.84 and 7.86 kcal/ml, respectively, which is the reverse of what one would expect based on power developed. Aircraft cannot compromise range due to the sensitivity of their missions. For this reason, energy content is equally important as MON values.

The current production volume of 100LL is approximately 850,000 gallons per day. 100LL has been designated by the Environmental Protection Agency (EPA) as the last fuel in the United States to contain tetraethyl lead. This exemption will likely come to an end in the near future.

Although discrete chemical compounds have been found to satisfy the motor octane number for 100LL octane aviation gasoline, they fail to meet a number of other technical requirements for aviation gasoline. This is true, for example, for isopentane, 90MON, and trimethyl benzene 136MON. For example, pure isopentane fails to qualify as an aviation fuel because it does not pass the ASTM specification D909 for supercharge ON, ASTM specification D2700 for motor octane number, and ASTM specification D5191 for vapor pressure. Pure sym-trimethylbenzene (mesitylene) also fails to qualify as an aviation fuel because it does not pass ASTM specification D2386 for freeze point, ASTM specification D5191 for vapor pressure, and ASTM specification D86 for the 10% distillation point.

It is of paramount importance that industry continues to progressively improve its environmental performance and lessen impacts to the global ecosystem, while continuing to reduce operating costs. Aviation recognizes these challenges must be addressed to ensure industry viability and is actively seeking to provide technologically driven solutions. Bio-derived jet fuel is a key element in the industry strategy to address these challenges.

Significant progress has been made in verifying the performance of Synthetic Paraffinic Kerosene (SPK) made from sustainable sources of bio-derived oils, after catalytic cracking and hydrogenation, that can be used in commercial aircraft at a blend ratio of up to 50 percent with traditional jet fuel (Jet A or JP-8).

Current alternative jet fuel certification targets are paraffinic alternative fuels used in 50/50 blends with conventional jet fuels, but the availability of synthetic aromatics (like mesitylene) enables the adjustment of the properties of paraffinic fuels, plus enables the potential of fully renewable fuels.

In addition, there is a significant amount of ongoing alternative aviation fuel research, both civilian and military, aimed at developing "drop-in" replacements for current petroleum-derived fuels. "Drop-in" means a fuel that is functionally equivalent to current fuels, requiring no aircraft hardware or handling changes.

Initial targets for certification of such fuels are Synthetic Paraffinic Kerosene (SPK) and Hydroprocessed Renewable Jet Fuel (HRJ), both as 50/50 with conventional petroleum-derived jet fuels. SPK and HRJ contain fully saturated linear alkanes in the $C_{12}$-$C_{22}$ range. These two processes typically produce a hydrocarbon jet fuel predominantly consisting of n-paraffins and iso-paraffins. Commercially, alternative fuels are added to ASTM D7566 when certified. These paraffinic fuels are not "drop-in" jet fuel for a number of reasons: first, their density falls below allowable 0.775-0.84 range; and second, they tend to cause fuel leaks through o-ring seals (due to the lack of aromatic components).

Currently, these shortcomings are avoided by blending the paraffinic fuels 50/50 with conventional jet fuels to gain the aromatic and cycloparaffinic components for density and seal swell. Extraction of the aromatic components in a typical jet fuel sample is illustrated in FIG. 1. Hydrocarbon type analysis (ASTM D2425) shows that most aromatics in jet fuels are substituted single-ring aromatics (typically about 15 vol %), with several percent additional of substituted napthalenes/tetralins/indanes (bicyclics). The abscissa in FIG. 1 is related to the molecular weight of the aromatics. The 38° C. minimum flash point in jet fuel eliminates most aromatics smaller than C8. In FIG. 2, a blend of commercial Exxon solvents (AR 100/150/200) has been used to simulate jet fuel aromatics in combustion testing which is used for comparison in a number of tests.

Therefore, tests have been carried out to evaluate synthetic aromatics used for jet fuels, including: first, the quantity of aromatics that must be added to SPK or HRJ fuels to create a fully-synthetic drop-in jet fuel; second, the effect of the added aromatic components on the seal swell; third, the effect of the aromatics on combustion performance; and fourth, the effects of added aromatics on other properties, such as lubricity.

Density, Flash Point, Freeze Point

Typical SPK and HRJ fuels have densities (in g/ml), and specific gravities in the range of 0.75-76 (at 16 C/standard conditions). However, the permissible jet fuel range is 0.775-0.84. Density has a large impact on range, and there is little interest in the aviation community in fuels with densities lower than 0.775.

FIG. 3 shows the result of adding mesitylene (density 0.8652) to Sasol® IPK (iso-paraffinic kerosene), one of the conventional SPK's with a density of 0.762. Addition of roughly 13 vol % mesitylene yields a Sasol® IPK/mesitylene fuel blend which meets the minimum density specification. The main objective of creating a fully synthetic biofuel can also be achieved by adding the bio-mesitylene to a conventional HRJ fuel. In a preferred embodiment, adding about 20 vol % bio-mesitylene to a tallow HRJ fuel (POSF 6308) yields a fuel having properties shown in Table 4.

It can be seen that adding mesitylene (flash point 44° C.) lowers the flash point of the HRJ slightly, but the minimum is 38° C., so there are no flash point issues for JP-8/Jet A/Jet A-1. Adding solely mesitylene to an HRJ will not meet the current JP-5 specifications (60° C. minimum flash). The low freeze point of mesitylene lowers the freeze point of the HRJ fuel. The density is well above the lower limit.

TABLE 1

Properties of 80 vol % tallow HRJ/20% mesitylene.

| | JP-8 req't | HRJ 6308 | 6308 + 20% mesitylene |
|---|---|---|---|
| Flash point, C. | >38 | 55 | 52 |
| Freeze point, C. | <−47 | −62 | −77 |
| Density | 0.775-0.84 | 0.758 | 0.779 |

Distillation/Boiling Range

There is a requirement for hydroprocessed SPKs in the current alternative fuel specification, ASTM D7566, for a minimum boiling range which is expressed in terms of the standard ASTM D86 boiling range limit as T90-T10>22° C. There is concern by engine manufacturing companies that very narrow boiling fuels (such as might be created by adding mesitylene to n-decane) might not have satisfactory combustor operability. Thus, adding a single-component aromatic component to a fuel (as opposed to a wide-boiling aromatics blend like FIG. 1) might not provide satisfactory properties. Therefore, in a preferred embodiment, the aromatic (such as mesitylene) was added only up to the jet fuel blend limit of 25 vol % at a maximum.

The 165° C. boiling point of the mesitylene tends to pull down the initial part of the boiling distribution. This can be seen in FIG. 4, where data for the 20% mesitylene blended into S-8 SPK is shown, along with several HRJs and blends (including three blends that have flown on commercial aircraft). As can be seen, several of the pure HRJs fall outside of JP-8 average range, which is the standard deviation around the 2006-2008 average of 5000 samples. However, it was unexpectedly discovered that blends (including 20% mesitylene in SPK) fall inside the typical JP-8 "experience base".

Seal Swell

Mesitylene was blended into an SPK fuel (Sasol® IPK) to determine the effects on the swell of nitrile o-rings (the "problem" o-rings for leaks). As shown in FIG. 5, mesitylene blends with the Sasol® IPK swelled slightly less than blends with petroleum aromatics (shown in FIG. 2) and 1,2,4-trimethylbenzene, but the difference within typical variations seen at a given aromatic level. In other words, a 15% mesitylene blend fell within the range of seal swells seen for jet fuels of the same aromatic content. Thus, it appears that the current 8% minimum aromatic level in ASTM D7566 will be adequate to ensure seal swell with mesitylene blends as well as SPK and HRJ blends.

Viscosity

There are two main concerns with viscosity of the fuel blend. First, maintaining viscosity below low temperature limits (e.g., 8 cSt at −20° C.) is required to ensure Auxiliary Power Unit (APU) and engine cold start performance. Second, use of jet fuel in diesel engines is enabled by a viscosity above 1.3 cSt at 40° C. As shown in FIG. 6, the low viscosity of the mesitylene decreases the viscosity at low temperatures (good for aircraft) and at high temperature (bad for diesels). Thus, meeting the 1.3 cSt requirement in mesitylene blends of roughly 10-15% is apparently achievable, but it is driven by the viscosity of the primary synthetic SPK or HRJ component.

Cetane

Use of jet fuel in diesel engines (either aviation or ground) requires an understanding of the effect of the jet fuel composition on cetane number as well as viscosity. A requirement of ASTM D975 is a minimum cetane number of 40 for diesel fuel, although cetane number is not specifically called out in ASTM D7566 at this point. Since cetane is roughly inversely proportional to octane, it is to be expected that adding mesitylene, a high-octane avgas blending component, would drop the cetane number of the base fuel. As shown in FIG. 7, this is indeed the case, where the addition of 20% mesitylene to a 57 cetane HRJ lowers the measured cetane (ASTM D6890) to about 44. However, this reduction tracks well with the general trend of cetane reduction with aromatic content in jet fuels, so it does not exclude the use of mesitylene blends in diesel engines.

Lubricity

Lubrication performance of jet fuel between fuel-wetted parts is an important property. One expected issue with fully-synthetic fuels is lubricity. The standard test for this property is ASTM D5001 the Ball on Cylinder Lubricity Evaluator (BOCLE). Jet fuel lubricity is general thought to come primarily from trace polar impurities in jet fuel, so it might be expected that existing fully-synthetic fuels would have poor lubricity (as indeed they do). The major issue for addition of synthetic aromatics to fuel blends is the effect of the aromatic addition on the poor lubricity of the base fuel.

It is expected that fully-synthetic fuels used by the military will contain the mandated corrosion inhibitor/lubricity improver (CI/LI) additive. Thus, a series of tests were performed with additized mesitylene/alternative fuel blends. As shown in FIG. 8, the lubricity of 10% mesitylene blends in various additized alternative base fuels falls well within the range of experience with JP-8 and meets the JP-8 lubricity requirements (the larger the wear scar, the poorer the lubricity). Very limited testing with fuel blends without the CI/LI additive were performed, and it was typically seen that mesitylene did not significantly affect the lubricity of the base fuel. For example, camelina HRJ had a BOCLE wear scar diameter of 0.76 mm, while addition of 10% mesitylene to the HRJ reduced the wear scar to 0.75 mm.

Combustion Emissions (Specifically Soot/Particulates)

The relationship between fuel aromatic content and soot/particulate emissions is well known. Thus, it would be a surprise if the addition of mesitylene did NOT increase soot from engines (or increase the smoke point, the relative specification test). Smoke point tests were performed on mesitylene blends with Sasol IPK. As shown in FIG. 9, the addition of mesitylene to this SPK fuel did, indeed, unexpectedly reduce the smoke point (equivalent to increasing soot emissions), but in a non-linear fashion. In any case, the results were well above the 22 mm specification limit. Efforts to verify this behavior led to inconsistent results, so it was decided to compare actual engines emissions in a T63 helicopter engine. In this case, the baseline JP-8 fuel contained 16 vol % aromatics, so the emissions from a 16% blend of mesitylene in the tallow HRJ fuel were compared to this baseline JP-8.

As shown in FIG. 10, the relatively low soot emissions implied in FIG. 9 are verified in this engine test. FIG. 10 shows the reduction in particulate (soot) emission index relative to the baseline 16% aromatic JP-8. As can be seen for the camelina and tallow HRJ fuels, the soot emission index is unexpectedly, dramatically reduced. 50/50 HRJ/JP-8 blends still show roughly 50% reductions. The 16% mesitylene blend also shows significant reductions relative to the JP-8 baseline at both idle and cruise conditions, so it seems clear that addition of mesitylene to alternative fuels does not produce a sooty fuel.

Thermal Stability

SPK and HRJ fuels are extremely thermally-stable fuels, due to their extremely low contaminant content. Thermal stability was assessed in various rig tests and in the Jet Fuel Thermal Oxidation Tester (JFTOT, ASTM D3241). The jet fuel specifications require that fuel pass the JFTOT at 260 C (the higher the temperature at which a fuel passes the test, the more stable the fuel). Fuels can also be characterized by where they fail the test, or "break"—hence the highest temperature at which a fuel will pass the test is known as its "breakpoint". A typical JP-8 breakpoint is 280° C.

The SPK and HRJ specifications require that these fuels pass the JFTOT at 325° C., at a minimum (thus the breakpoint is above 325° C.). This temperature is well above that for typical jet fuels, verifying the high thermal stability. A limited amount of thermal stability testing was performed with mesitylene, with more extensive testing performed with the aromatic blend shown in FIG. 2. Many aromatics are known to reduce fuel thermal stability although some appear to be relatively benign. In a series of tests with petroleum aromatics in various HRJ and SPK fuels, it was discovered that addition of 10, 15 and 20 vol % petroleum aromatics consistently reduced the breakpoint from >325° C. to about 280° C. for all the fuels (thus little affect of aromatic content).

Therefore, addition of petroleum aromatics above some low threshold (below 10%) reduces the thermal stability of SPK and HRJ fuels to typical jet fuel values (where the average aromatic content is 15-20%). The behavior was seen with mesitylene, where 10% mesitylene in the Syntroleum® S-8 SPK fuel dropped the breakpoint down to about 280° C., or typical jet fuel levels (similar to petroleum aromatics).

The fermentation of a biomass using microbes to produce acetone and butanol was first discovered by Chaim Weizmann in 1916 and is described in U.S. Pat. No. 1,315,585 and other corresponding patents throughout the world. This process known as the Weizmann process was used by both Great Britain and the United States in World Wars I and II to produce acetone for the production of cordite used in making smokeless powder. Unfortunately, this method is energy intensive, and accordingly uneconomical.

A number of methods are known for making mesitylene from acetone and include, for example:

(1) Liquid phase condensation in the presence of strong acids, e.g. sulfuric acid and phosphoric acid as described in U.S. Pat. No. 3,267,165 (1966);

(2) Vapor phase condensation with tantalum containing catalysts as described in U.S. Pat. No. 2,917,561 (1959);

(3) Vapor phase condensation using as catalyst the phosphates of the metals of group IV of the periodic system of elements, e.g. titanium, zirconium, hafnium and tin as described in U.S. Pat. No. 3,946,079 (1976);

(4) Vapor phase reaction in the presence of molecular hydrogen and a catalyst selected from alumina containing chromia and boria as described in U.S. Pat. No. 3,201,485 (1965);

(5) Vapor phase reaction using catalysts containing molybdenum as described in U.S. Pat. No. 3,301,912 (1967) or tungsten as described in U.S. Pat. No. 2,425,096, a vapor phase reaction over a niobium supported catalyst with high selectivity. The catalyst is preferably made by impregnating a silica support with an ethanolic solution of $NbCl_5$ or an aqueous solution of Nb in order to deposit 2% Nb by weight and by calcining the final solid at 550° C. for 18 hours. At 300° C., the condensation of acetone produces mainly mesitylene (70% selectivity) at high conversion (60-80% wt) as described in U.S. Pat. No. 5,087,781.

It is also known in the art to dimerize acetone to ultimately form isopentane. This process involves first dimerizing acetone to form diacetone alcohol which is then dehydrated to form mesityl oxide. The mesityl oxide then undergoes gas phase reformation/hydrogenation to form isopentane.

It is also known from U.S. Pat. No. 7,141,083 to produce a fuel comprising mesitylene and straight-chain alkanes (i.e., hexanes, heptanes, octanes, nonanes and the like) from plant oil, such as corn oil. The composition of corn oil is shown in Table 1 below. The predominant components of corn oil are stearic, palmitic, oleic, and linoleic acids of the free fatty acids.

It is an object of the present invention to provide biogenic fuels that effectively replace petroleum-based fuels currently used in engines.

It is another object of the present invention to provide fully renewable fuels for other internal combustion/heat engines as well.

It is a further object of the present invention to provide high energy renewable fuels for use in turbines and other heat engines by the same methodology; the energy content and physical properties of the renewable components being tailored to the type of engine to be fueled.

It is another object of the present invention to provide a method of producing this biogenic fuel.

It is another object of the present invention to provide a non-petroleum based aviation fuel which meets the technical specifications of ASTM International for petroleum-based turbine fuels.

It is still another object of the present invention to provide a process for the production from a biomass of the components of binary chemicals and ternary mixtures which satisfy the technical specifications for both turbine and diesel engines.

SUMMARY OF THE INVENTION

In order to achieve the objects of the present invention, the present inventors have arduously carried out research and endeavored to provide a method for producing mesitylene-isopentane fuel, preferably derived from a biomass having a high energy content. Accordingly, in a first preferred embodiment of the present invention, the present inventors provide a method of producing a mesitylene-isopentane fuel, comprising:

(a) in a gas phase reaction passing acetone in contact with a catalyst at a temperature of from about 250 to 400° C., at a liquid hourly space velocity of from about 1 to 8, and at a pressure of from about 50 to 200 psi, said catalyst comprising from about 0.5 to 10 wt % of one or more metal oxides selected from the group consisting of vanadium oxide, niobium oxide, and tantalum oxide obtained from water soluble salts thereof, whereby to form reaction products in which a portion of the acetone feed is trimerized to form mesitylene, and the remainder of acetone feed is either dimerized to form mesityl oxide or other by-products;

(b) separating the mesitylene from other reaction products;

(c) converting said mesityl oxide in a series of reactions to isopentane by subjecting the mesityl oxide of step (a) to dehydration, demethylation, and hydrogenation; and (d) mixing the separated mesitylene from step (b) with the isopentane obtained from step (c).

In a second preferred embodiment of the present invention, there is provided in the first preferred embodiment a method wherein acetone contacts the catalyst at a temperature of from about 275 to 375° C., at a liquid hourly space velocity of from about 2 to 8, and at a pressure of from about 75 to 175 psi.

In a third preferred embodiment of the present invention, there is provided in the first preferred embodiment a method wherein the catalyst comprises from about 0.5 to 7.0 wt % of metal oxide.

In a fourth preferred embodiment of the present invention, there is provided in the first preferred embodiment a method wherein the water soluble salts comprise one or more of vanadium oxalate, niobium oxalate, and tantalum oxalate.

In a fifth preferred embodiment of the present invention, there is provided in the first preferred embodiment a method wherein after the metal oxides are impregnated on the acidic silicon-based substrate, the impregnated substrate is calcined at a temperature of from about 250 to 350° C. for a period of from about 11 to 22 hours.

In a sixth preferred embodiment of the present invention, there is provided in the first preferred embodiment a method wherein said mesityl oxide in step (c) is subjected to a dehydration reaction to form as reaction products methyl isopropenyl acetylene and 4-methyl-1,2,4 pentatriene.

In a seventh preferred embodiment of the present invention, there is provided in the sixth preferred embodiment a method wherein reaction products from the dehydration reaction are subjected to a demethylation reaction to form as reaction products of isopropenyl acetylene and/or 1,2,4 pentatriene.

In an eighth preferred embodiment of the present invention, there is provided in the seventh preferred embodiment a method wherein the isopropenyl acetylene and/or 1,2,4 pentatriene are all subjected to hydrogenation to form isopentane.

In a ninth preferred embodiment of the present invention, there is provided in the first preferred embodiment a method wherein the acetone is derived from:

(a) fermenting a biomass to produce a mixture of metabolites comprising acetone and butanol; and (b) separating the acetone from butanol and any ethanol or other solvents in the mixture by fractional distillation.

In a tenth preferred embodiment of the present invention, there is provided in the sixth preferred embodiment a method wherein the acetone is derived from:

(a) fermenting a biomass to produce a mixture of metabolites comprising acetone and butanol; and (b) acetone from butanol and any ethanol or other solvents in the mixture by fractional distillation.

In an eleventh preferred embodiment of the present invention, there is provided in the seventh preferred embodiment a method wherein the acetone is derived from (a) fermenting a biomass to produce a mixture of metabolites comprising acetone and butanol; and (b) separating the acetone from butanol and any ethanol or other solvents in the mixture by fractional distillation.

In a twelfth preferred embodiment of the present invention, there is provided in the eighth preferred embodiment a method wherein the acetone is derived from (a) fermenting a biomass to produce a mixture of metabolites comprising acetone and butanol; and (b) separating the acetone from butanol and any ethanol or other solvents in the mixture by fractional distillation.

In a thirteenth preferred embodiment of the present invention, there is provided in the first preferred embodiment a method wherein the reaction products from step (a) are first subjected to a phase separation and then a fractional distillation to separate resultant mesitylene from other reaction products.

In a fourteenth preferred embodiment of the present invention, there is provided in the first preferred embodiment a method wherein liquid effluent from step (a) above is fed into a phase separator where it is separated into two phases, an aqueous and an organic phase.

In a fifteenth preferred embodiment of the present invention, there is provided in the fourteenth preferred embodiment a method wherein the aqueous layer is then stripped of any remaining unreacted acetone, that is fed back into the reaction in step (a) above.

In a sixteenth preferred embodiment of the present invention, there is provided in the fifteenth preferred embodiment a method wherein the organic phase is fed into a distillation column where mesitylene oxide and other by-products are recovered.

In a seventeenth preferred embodiment of the present invention, there is provided a method of producing a mesitylene-isopentane fuel, comprising:

(a) in a gas phase reaction passing acetone in contact with a catalyst at a temperature of from about 250 to 400° C. and the liquid hourly space velocity of from about 1 to 8, and at a pressure of from about 50 to 200 psi, said catalyst comprising from about 0.5 to 10 wt % of one or more metal oxides selected from the group consisting of vanadium oxide, niobium oxide, and tantalum oxide obtained from water soluble salts thereof, whereby to form reaction products in which a portion of the acetone feed is trimerized to form mesitylene, and the remainder of acetone feed is either dimerized to form mesityl oxide or other by-products;

(b) feeding liquid effluent from the reaction in step (a) above into a phase separator where it is separated into two phases, an aqueous and an organic phase;

(c) stripping the aqueous layer of any remaining unreacted acetone, that is fed back into the reaction in step (a) above;

(d) passing the organic phase into a distillation column where mesitylene, mesityl oxide and other by-products are recovered;

(e) passing recovered mesitylene from step (d) to a holding tank;

(f) converting said mesityl oxide in a series of reactions to isopentane by subjecting the mesityl oxide of step (a) to dehydration, demethylation, and hydrogenation; and (g) mixing the separated mesitylene from step (e) with the isopentane obtained from step (f).

In an eighteenth preferred embodiment of the present invention, there is provided in the seventeenth preferred embodiment a method wherein said mesityl oxide in step (f) is subjected to a dehydration reaction to form as reaction products methyl isopropenyl acetylene and 4-methyl-1,2,4 pentatriene.

In a nineteenth preferred embodiment of the present invention, there is provided in the eighteenth preferred embodiment a method wherein said methyl isopropenyl acetylene and 4-methyl-1,2,4 pentatriene are subjected to a demethylation reaction to form as reaction products isopropenyl acetylene and/or 1,2,4 pentatriene.

In a twentieth preferred embodiment of the present invention, there is provided in the nineteenth preferred embodiment a method wherein reaction products from the isopropenyl acetylene and/or 1,2,4, pentatriene are subjected to hydrogenation to form isopentane.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
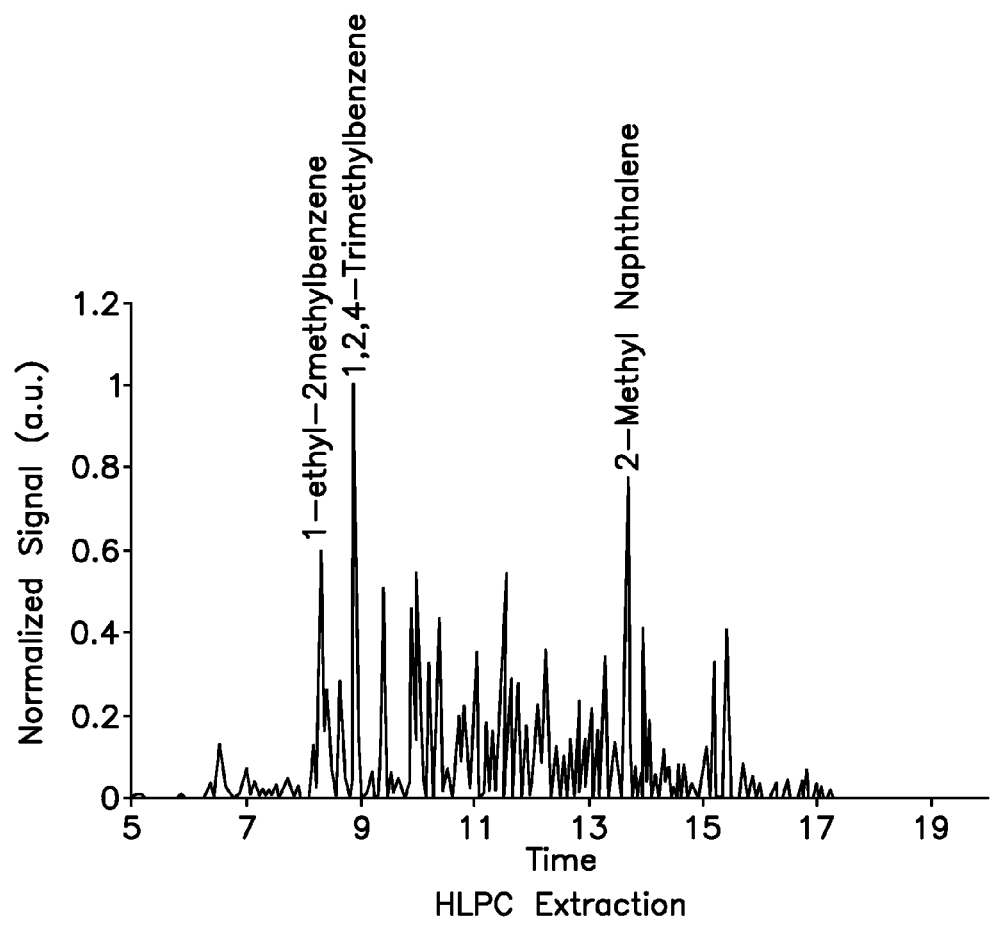
FIG. 1 is a graph for HLPC Extraction, illustrating a typical JP-8 aromatics extracted from conventional jet fuel.
Figure 2:
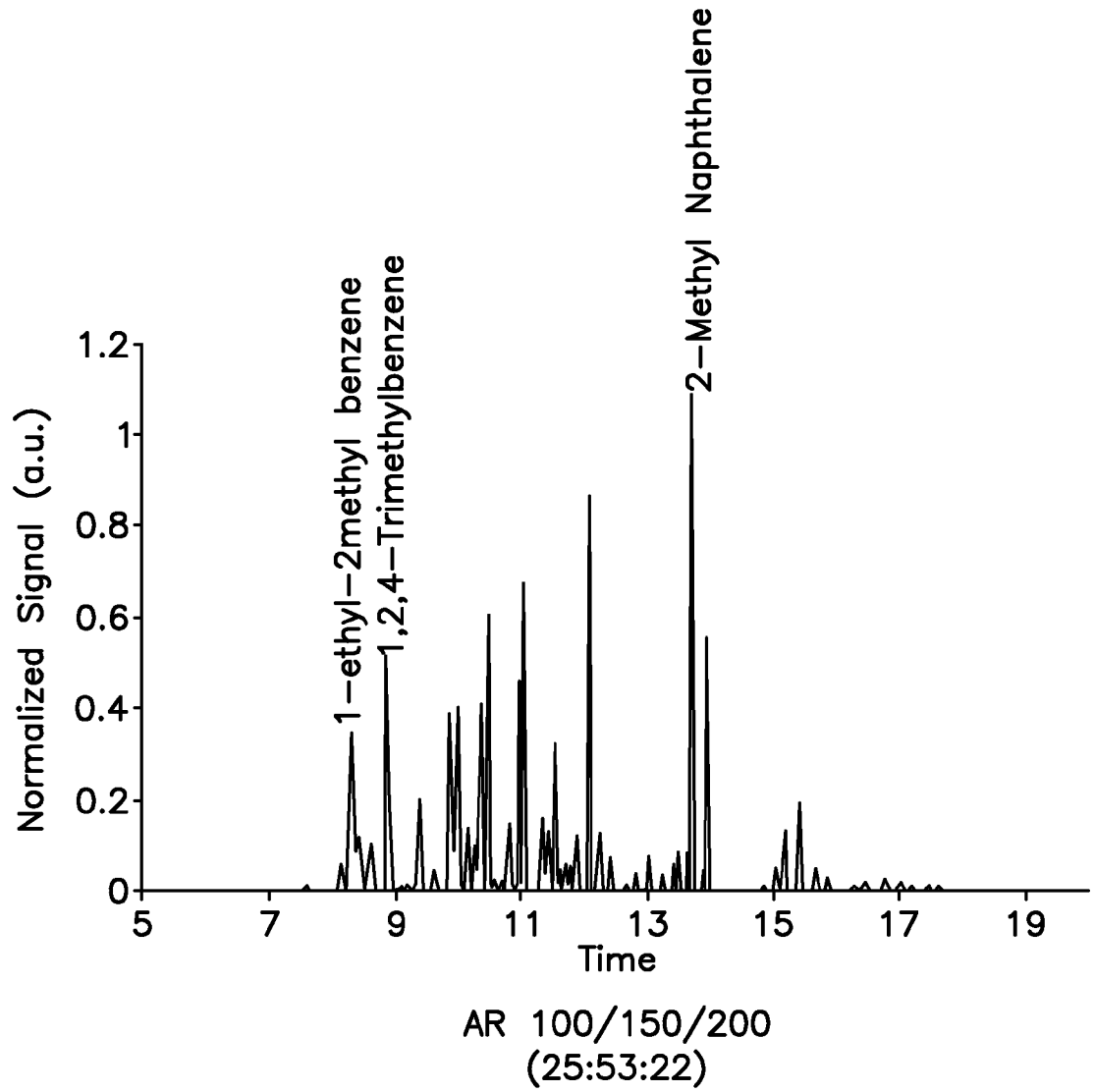
FIG. 2 is a graph illustrating a solvent blend simulation of jet fuel aromatics. (Exxon® AR 100, 150, 200).
Figure 3:
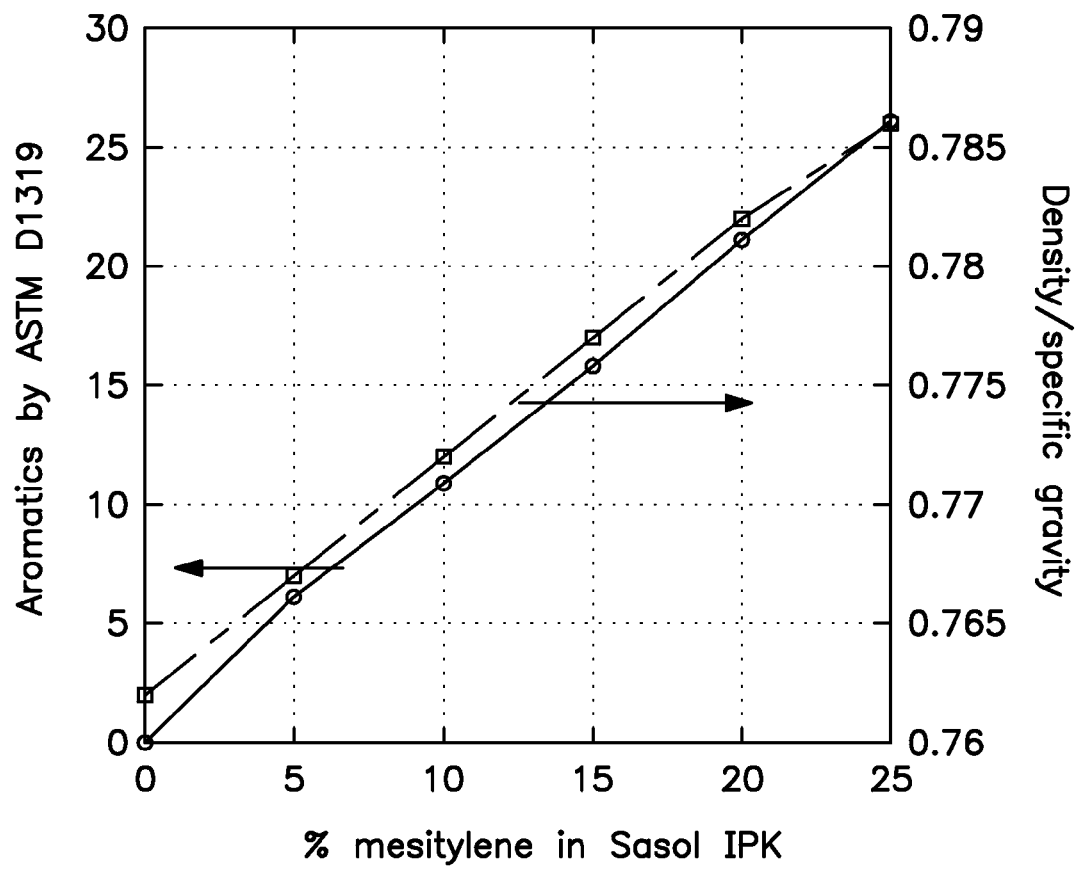
FIG. 3 is a plot of aromatics by ASTM D1319 versus % mesitylene in Sasol® IPK, illustrating the density of mesitylene/SPK blends.
Figure 4:
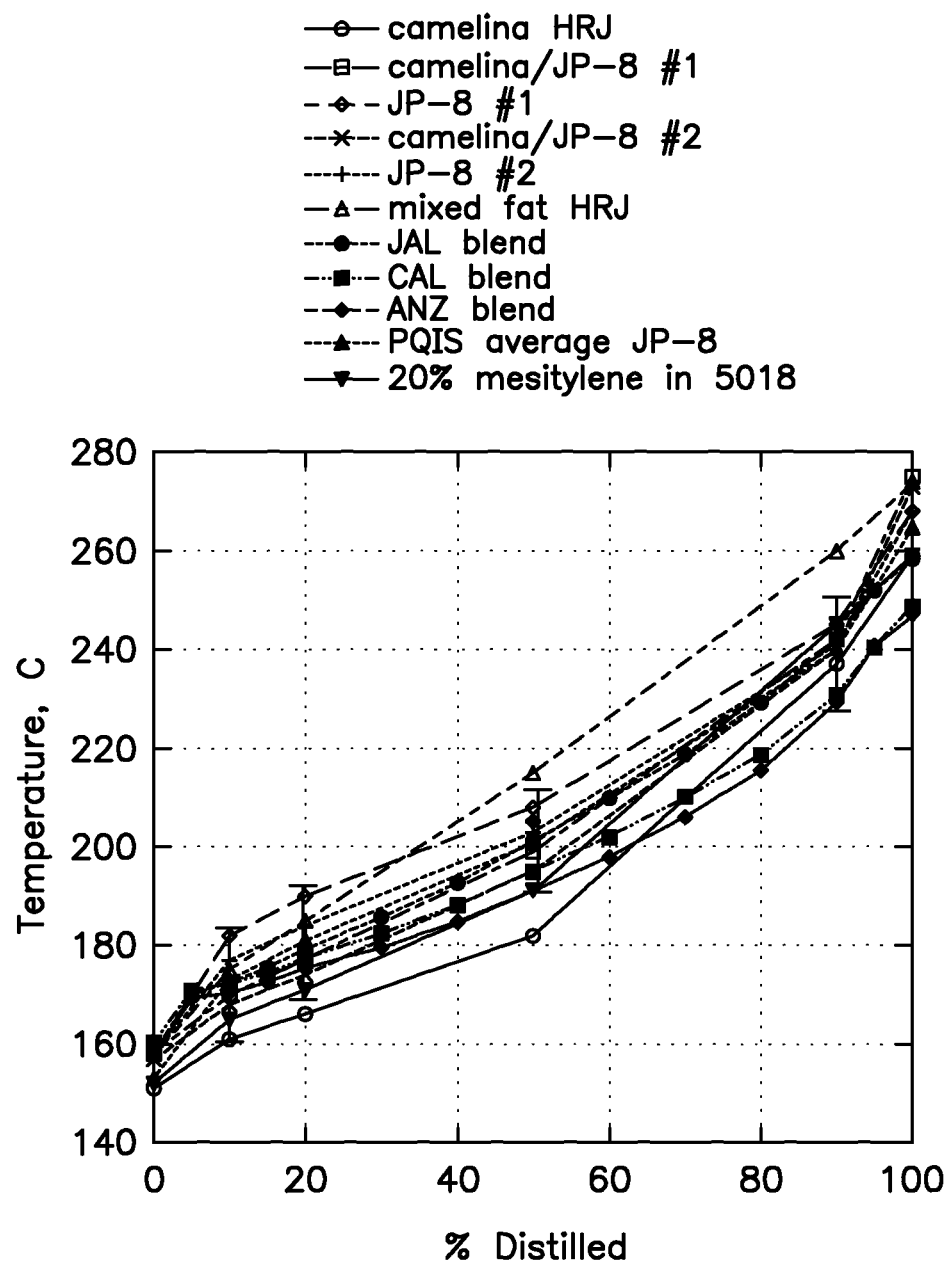
FIG. 4 is a plot of temperature versus % distilled providing distillation data for various fuels and blends.
Figure 5:
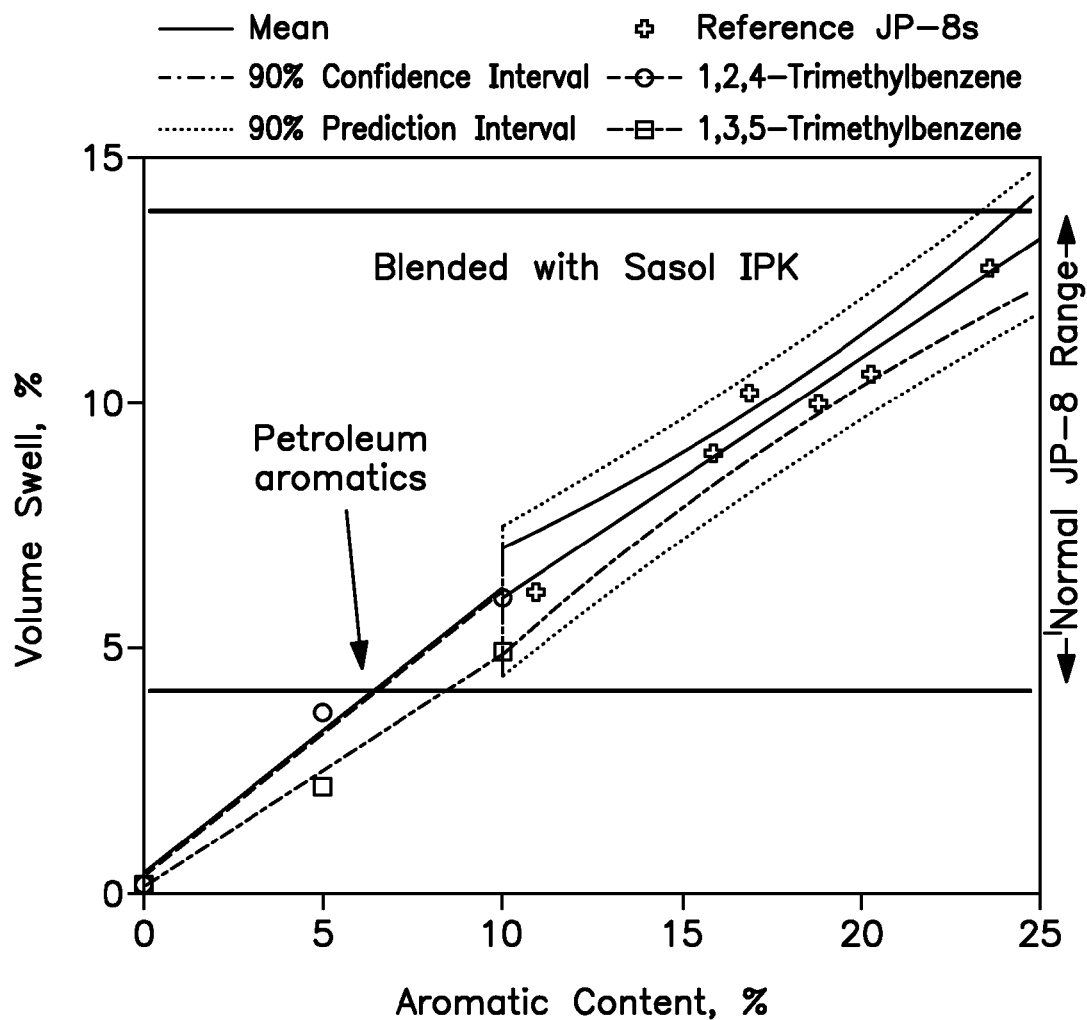
FIG. 5 is a graph of volume swell versus aromatic contents, illustrating nitrile o-ring seal swell data for mesitylene/SPK blends.
Figure 6:
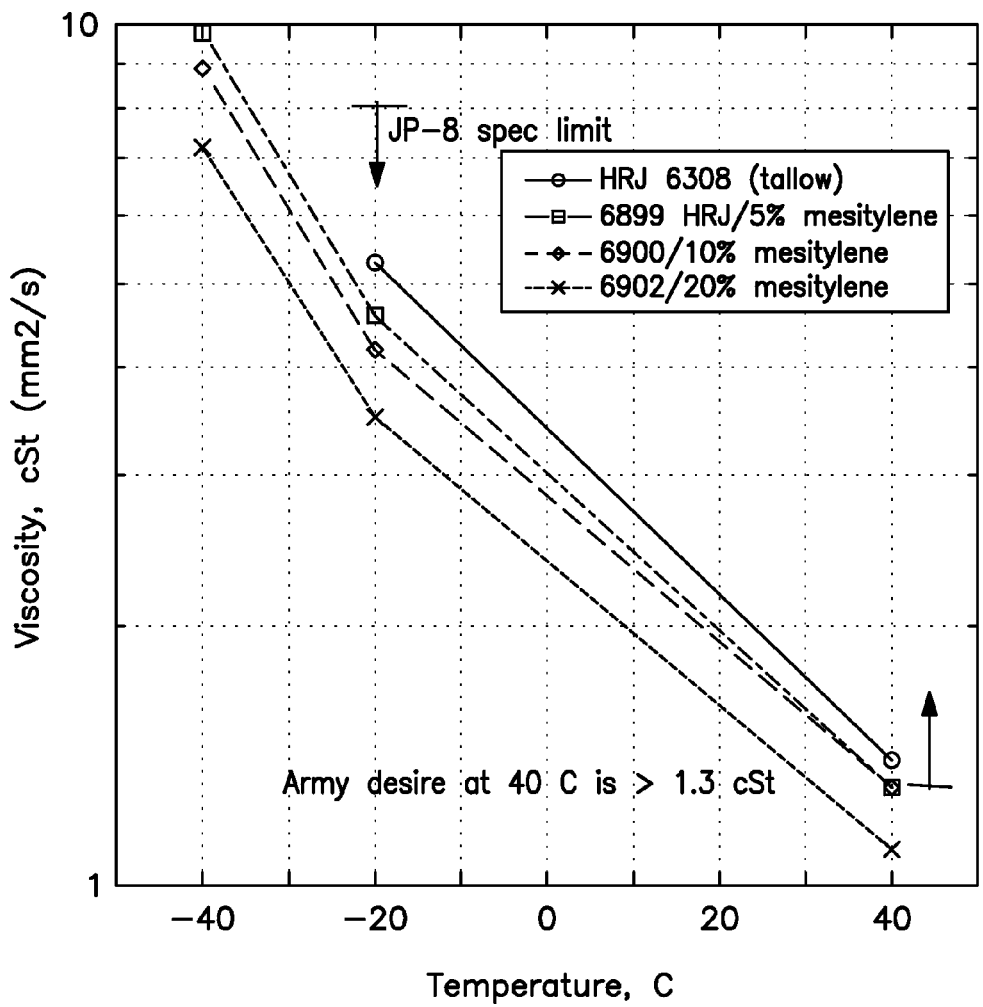
FIG. 6 is a graph of viscosity versus temperature, illustrating the viscosity of mesitylene blends in tallow HRJ.
Figure 7:
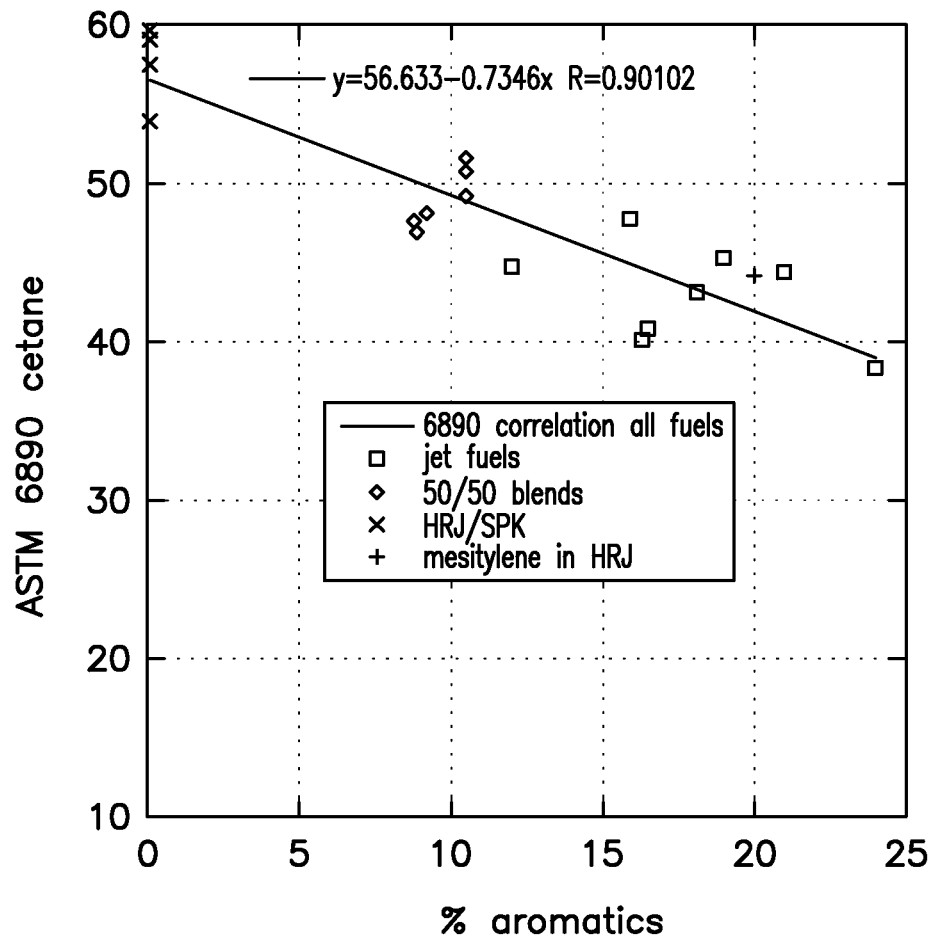
FIG. 7 is a plot of ASTM 6890 cetane versus % aromatics, illustrating measured cetane values for various jet fuel blends.
Figure 8:
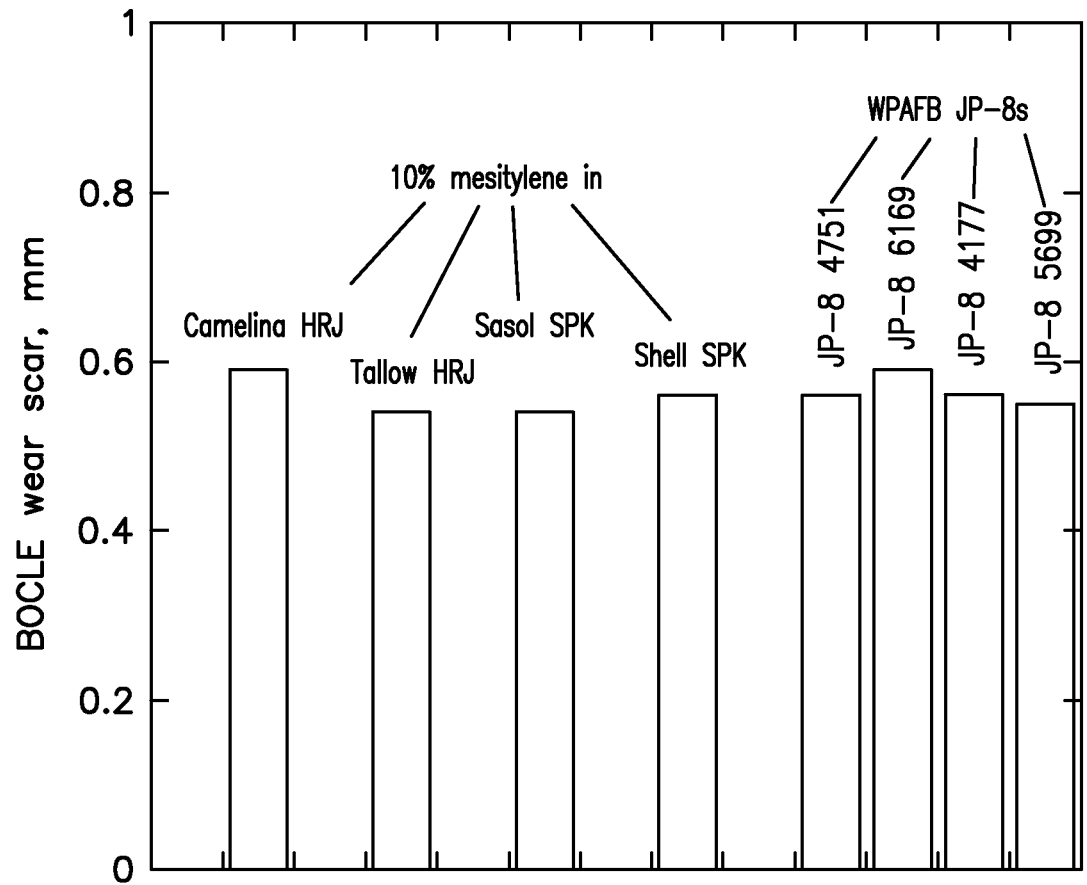
FIG. 8 is a bar chart of BOCLE wear scar, illustrating lubricity results for fuels and various blends.
Figure 9:
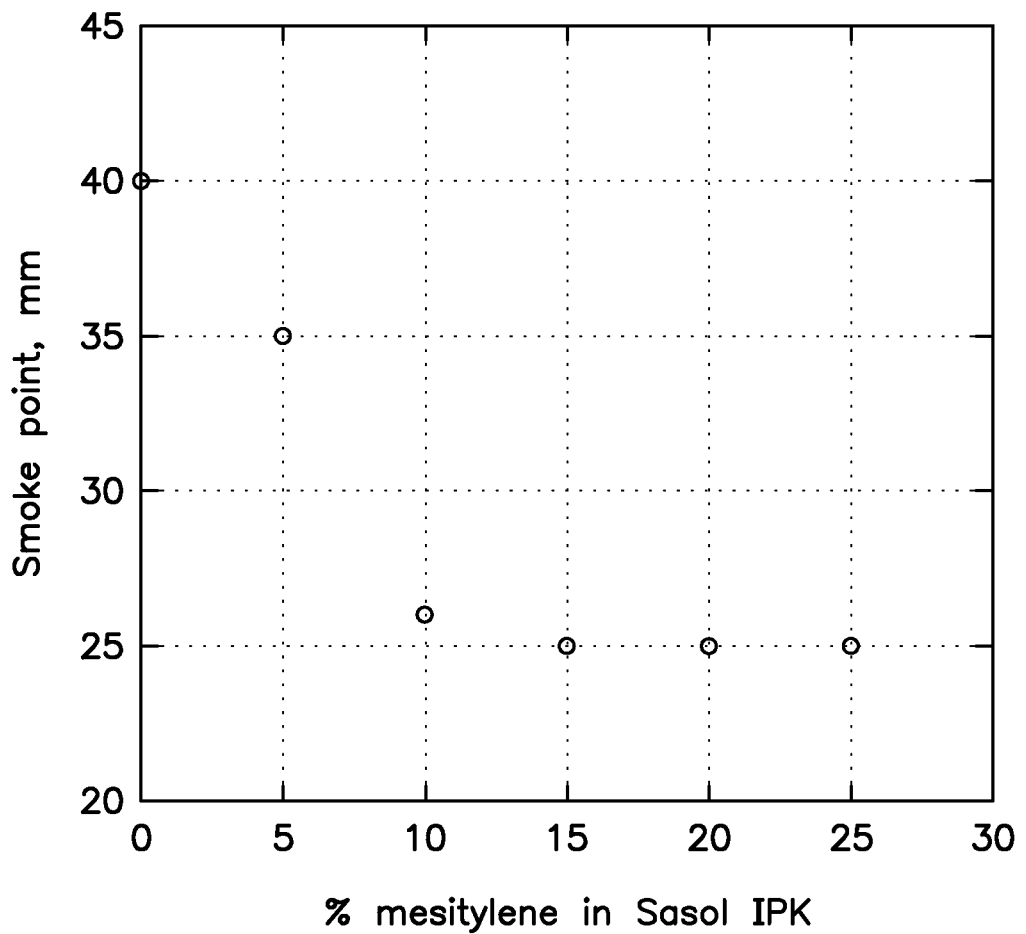
FIG. 9 is a plot of smoke point versus % mesitylene in Sasol® IPK.
Figure 10:
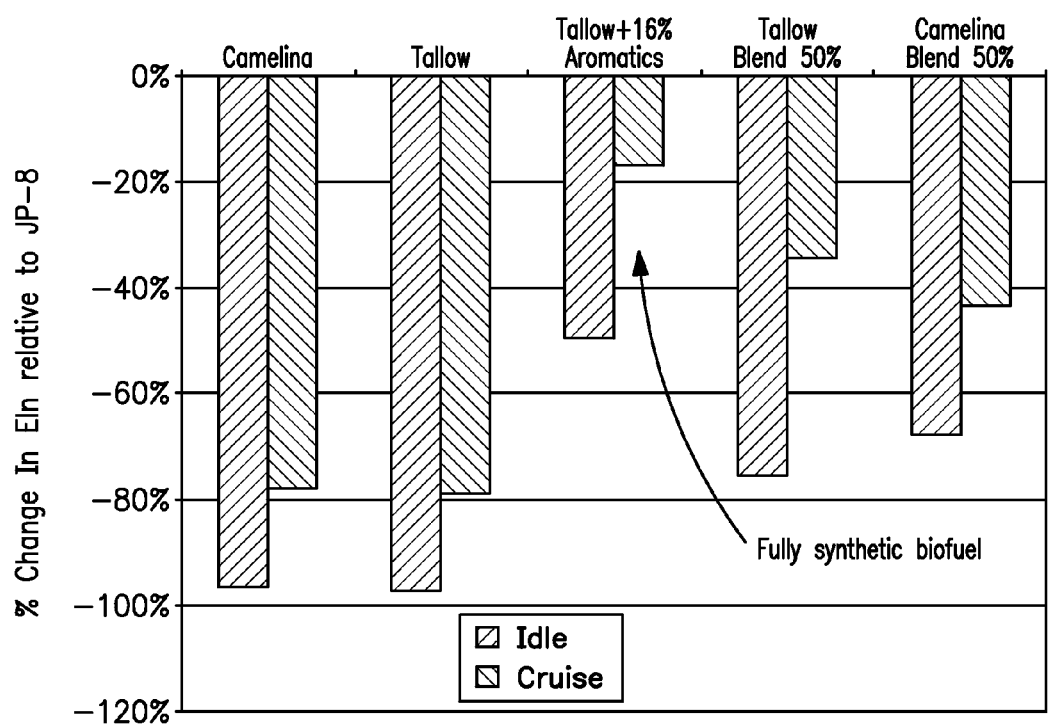
FIG. 10 is a bar chart showing % change in emission index ($E_{in}$) relative to JP-8, illustrating particulate soot emissions index changes (relative to a 16% aromatic JP-8 baseline) for various HRJ fuels and blends.

As discussed above, the present invention provides a non-petroleum-based renewable fuel comprised of fully renewable components, i.e., components derived from bio-sources such as corn. This fuel has several variants, the preferred variants being turbine fuel and diesel fuel. Advantageously, the components of the fuels discussed above are all derivable from plant or animal oils, and the product can be tailored to the input stock. In general, plant oils are preferred due to their lower molecular weight products.

Both the turbine fuels and the diesel fuels of the present invention provide an overall mix and match with discreet components derivable from all plant or animal oils, and the product can be tailored to the input stock. In general, plant oils are preferred as the base stock for production of the fuel component of the composition, due to their lower molecular weight products. With regards to same, the fuel component can be derived from various plant source bio-oils. For example, the bio-oil may include soybean oil, rapeseed oil, canola oil or corn oil, palm oil, and combinations thereof. Most preferably, corn oil is utilized as the bio-oil component because of its enhancement of energy, fuel's physical properties, and lubricity properties. Corn oil is derived directly from the corn germ. The components of corn oil are shown below in Table 2.

TABLE 2

| FFA | C Number | Unsaturation | As is |
|---|---|---|---|
| Lauric | 12 | 0 | 0% |
| Myristic | 14 | 0 | 0.06% |
| Palmitic | 16 | 0 | 13.81% |
| Palmitoleic | 16 | 1 | 0.19% |
| Margaric | 17 | 0 | 0.07% |
| Stearic | 18 | 0 | 2.19% |
| Oleic | 18 | 1 | 27.86% |
| Linoleic | 18 | 2 | 52.41% |
| a-Linoleic | 18 | 3 | 1.29% |
| Arachidic | 20 | 0 | 0.45% |
| Eicosenoic | 20 | 1 | 0.35% |
| Eicosadienoic | 20 | 2 | 0.04% |
| Behinic | 22 | 0 | 0.19% |
| Erucic | 22 | 1 | 0.00% |
| Ligoceric | 24 | 0 | 0.24% |
| Others | | | 1.00% |

With reference to Table 2, it can be seen that corn oil contains derivable straight-chain alkanes, namely, n-octadecane and n-hexadecane. Also, it is known that these two alkanes can be cracked to form n-nonane and n-octane, respectively. Also, triacylglycerides are comprised of these fatty acids, compositions shown in Table 2 above. Part of the JetE (and others) thermolysis process is the generation of propane from the triacylglycerides as well.

It is also known that propane can be dehydrogenated to form propyne and hydrogen (which the thermolysis process needs). Propyne can be directly trimerized to mesitylene via the same catalysts used for trimerizing and dehydrating acetone to form mesitylene. It can thus be seen that bio-oils can be used to produce mesitylene, n-octadecane, n-hexadecane, n-nonane, and n-octane.

With regards to the aromatic hydrocarbon component of these fuels, unlike conventional petroleum-based fuels, the present invention comprises aromatic hydrocarbons derived from acetone, a fully renewable source. Most preferably, the aromatic hydrocarbon is mesitylene. Mesitylene can conveniently be prepared by the trimerization of acetone or propyne; acetone can be readily prepared from biomass, and propyne can be extracted from natural gas. Mesitylene is preferred, since the acetone or propyne reaction "stops" at the trimer, which makes the conversion high due to lack of significant side-reactions. Mesitylene can be used as an octane and energy enhancing ingredient.

With regards to the straight chain alkanes, the alkanes are preferably derived from biomass, specifically oils derived from biomass. Straight chain alkanes have the lowest octane number of a given set of alkane isomers; the more branched the molecule, the smoother combusting (higher octane) the molecule exhibits when tested. Preferred straight chain alkanes are utilized in the fuels of the present invention including tetradecane, heptane, octadecane, octane, and nonane. These straight chain alkanes act as octane depressants within the fuel.

Lower straight chain alkanes such as n-pentane, n-butane, propane, and below, have too low of a boiling point to be useful as a main component of the fuels of the present invention. Higher straight chain alkanes, such as n-nonane, n-decane and above, have a high carbon-to-hydrogen molecule fraction (>0.444). Straight chain alkanes can be used to suppress the octane of a given fuel, while maintaining a high energy content per unit volume. Higher alkanes can be used in diesel and jet turbine applications.

Turbine Fuels:

In particular, when the fuel is tailored to turbine engine application, a first renewable turbine fuel comprising two components is provided, namely from 50-99 wt % mesitylene and from 1-50 wt % of one more alkanes, more preferably 75-85 wt % of mesitylene and 10-40 wt % of tetradecane, even more preferably 75-85 wt % of mesitylene and 15-25 wt % of tetradecane, most preferably 80 wt % of mesitylene and 20 wt % of tetradecane.

For turbine applications, if the mesitylene is present in an amount of less than 45 wt %, the freezing point will fall out of specification. Further, if the amount of alkanes, such as tetradecane, is less than 1 wt %, the fuel will be too dense and will not possess a high enough specific energy (net heat of combustion per mass). However, if the amount of alkanes in the turbine fuel composition exceeds 50 wt %, the freezing point will fall out of specification.

In a further embodiment of the present invention, a second renewable turbine fuel comprising three components is provided, namely, from about 1 to 65 wt % of mesitylene, from about 5 to 60 wt % of n-tetradecane or, preferably 5-60 wt % of n-hexadecane, and from about 15 to 75 wt % of heptane. In a preferred embodiment, the second renewable turbine fuel comprises 5 to 55 wt % of mesitylene, from about 5 to 55 wt % of n-tetradecane or, preferably 5-55 wt % of n-hexadecane, and from about 20 to 65 wt % of heptane.

In a more preferred embodiment, the second renewable turbine fuel comprises 5 to 48 wt % of mesitylene, from about 15 to 45 wt % of n-tetradecane or, preferably 15-45 wt % of n-hexadecane, and from about 32 to 60 wt % of heptane. In a highly preferred embodiment, the second renewable turbine fuel comprises 45 wt % of mesitylene, 17.5 wt % of n-tetradecane or, preferably 17.5 wt % of n-hexadecane, and 50 wt % of heptane. In another highly preferred embodiment, the second renewable turbine fuel comprises 10 wt % of mesitylene, 40 wt % of n-tetradecane or, preferably 50 wt % of n-hexadecane, and 50 wt % of heptane.

In this turbine fuel application, if the mesitylene is present in an amount of less than 1 wt %, then the fuel will fall below the specified density range, will not provide the necessary specific energy per gallon, and may not meet the freezing point specification, whereas if the mesitylene is present in an amount greater than 65 wt %, then the density will be outside the high end of the specified range and the net heat of combustion by mass will fall below the specified limit. Further, if the amount of alkane, such as tetradecane, is less than 5 wt %, the fuel composition will possess a net heat of combustion by mass that is too low, whereas if the alkane is present in an amount greater than 50 wt %, then the freezing point of the fuel will be too high and the density will fall below the specified range.

In addition, the heptane component, which is preferably n-heptane, provides a large decrease in freezing point and a high net heat of combustion by mass. If heptane is present in an amount of less than 15 wt %, then the fuel may possess too high a freezing point, whereas if the amount of heptanes exceeds 74 wt %, then the density will be too low and the specific energy per gallon will be significantly decreased, resulting in fewer "miles per gallon" out of the fuel.

In the above two turbine fuel formulations, mesitylene is added for the high energy per gallon, and to maintain the density (up) to within required ASTM specifications. One of the preferred ternary turbine formulations comprises about 10 wt % mesitylene, about 40 wt % n-tetradecane, and about 50 wt % n-heptane. In this formulation, it was found that this weight percent of mesitylene kept the density from getting too low; n-tetradecane was found to provide the formulation with a high energy per pound; and n-heptane was found to keep the freezing point of the composition down to within specifications (as well as provide a very high energy per pound).

Further, as mentioned above, in a preferred embodiment, n-hexadecane can be used in place of n-tetradecane, and n-octane can be used in place of n-heptane, in this biogenic fuel.

To test the characteristics of the turbine fuels of the present invention, the present inventor prepared three test compositions, denoted below in Table 3 as Turbine Test Fuel A, B and C, respectively. Then, the physical properties of each test fuel composition were determined using standard accepted methods, namely the test methods used in ASTM D1655, which is the specification for Jet A and Jet A-1 Aviation Turbine Fuels.

TABLE 3

|  | Turbine Test Fuel A | Turbine Test Fuel B | Turbine Test Fuel C |
| --- | --- | --- | --- |
| Mesitylene (wt %) | 80.0 | 45.0 | 10.0 |
| Heptane (wt %) | 0.0 | 37.5 | 50.0 |
| Tetradecane (wt %) | 20.0 | 17.5 | 40.0 |
| Boiling Point (° K) | 454.8 | 427.8 | 438.7 |
| Freezing Point (° K) | 235.6 | 218.4 | 225.3 |
| Cetane Number (CN) | 31.2 | 44.6 | 67.9 |
| Net Heat Of Combustion (MJ/kg) | 41.61 | 42.87 | 43.99 |
| Net Heat Of Combustion (MJ/L) | 35.15 | 33.41 | 32.27 |
| Density (g/cc) | 0.8447 | 0.7793 | 0.7335 |

As illustrated above, the test turbine fuels of the present invention have net heats of combustion that vary greatly. Turbine Test Fuel B is what most closely matches current Jet A, based on the ASTM D1655 specification. All properties fall within the parameters of that specification. Turbine Test Fuel A should provide 5% greater energy per gallon compared to 'average' Jet A because of the higher net heat of combustion by volume. This results in extended range of the aircraft using this fuel. The freezing point of this fuel is outside of, but within 3° C. of, the maximum freezing point limit of D1655, and the density is within 0.005 g/cc of the maximum density limit.

This causes the fuel to not meet the specification, but an additive may be included before reaching the end user to correct those small deficiencies. Turbine Test Fuel C has a high net heat of combustion by mass and a low density. This means that the fuel will be significantly lighter than current turbine fuel; weight savings are always important in aviation. The lower net heat of combustion by volume, however, results in less range per gallon.

Diesel Fuels

In a further embodiment of the present invention, a renewable (biogenic) diesel fuel is provided which, like the above first and second renewable turbine fuels, may be comprised of two or three components, namely mesitylene and two alkanes. However, specifically, in the case of diesel fuels with high energy per gallon, n-octadecane is preferably used in place of n-tetradecane because of the higher density and increased net heat of combustion by volume. Further, n-octane or n-nonane is used in place of n-heptane in the diesel application for the same reasons. Like the above turbine fuels, mesitylene is provided in the diesel fuel to provide high energy per pound.

To confirm the characteristics of the diesel fuel composition of the present invention, two diesel test fuels, denoted as Diesel Test Fuel A and B, respectively, were prepared. The physical characteristics of same were then tested using standard accepted methods, which are listed in ASTM D975, the specification for all diesel fuel oils. The results of these tests are shown below in Table 4 below.

TABLE 4

|  | Diesel Test Fuel A | Diesel Test Fuel B |
| --- | --- | --- |
| Mesitylene (wt %) | 70 | 35 |
| Octane (wt %) | 0 | 50 |
| Octadecane (wt %) | 30 | 15 |
| Boiling Point (° K) | 483.3 | 441.0 |
| Freezing Point (° K) | 247.7 | 232.0 |
| Cetane Number (CN) | 43.5 | 53.8 |
| Net Heat Of Combustion (MJ/kg) | 41.88 | 43.15 |
| Net Heat Of Combustion (MJ/L) | 34.77 | 33.23 |
| Density (g/cc) | 0.8303 | 0.7701 |

As illustrated above, the test turbine fuels of the present invention vary greatly in composition and energy content like the turbine fuels after which they are modeled. Diesel Test Fuel A has a much higher net heat of combustion by volume, leading to an increased range per gallon when operated in a compression-ignition engine. Diesel Test Fuel B has a lower freezing point, allowing for this fuel to be used in colder climates without fear of freezing in the fuel tank.

It was unexpectedly discovered by the present inventors that, by combining the components in the weight ranges called for herein in the fifteenth and twenty-third preferred embodiments herein, a completely non-petroleum-based diesel fuel, fully derivable from renewable biomass sources, could be obtained. Further, it was discovered that the diesel fuel components could be conveniently adjusted to produce an appropriate air to fuel ratio for application in a heat engine. Further, it was unexpectedly discovered that this renewable diesel fuel can be formulated to have very desirable properties by varying the alkane ingredients, with the energy increasing components such as mesitylene.

Alternatively, as called for in the present invention, the present inventors unexpectedly discovered that the renewable diesel fuel of the present invention can be formulated to have a much lower freezing point, as low as 232° K. This is achieved by adding octane or nonane, both which have an extremely low freezing point, up to 60 wt %. Additions above that level may decrease the net heat of combustion by volume, and therefore the miles per gallon achievable, too much to be practical. Accordingly, the renewable diesel fuel of the present invention can be utilized in very cold climates. In addition, the diesel fuel composition of the present invention, preferably containing octadecane and/or octane, possesses sufficiently high energy and cetane number needed for satisfactory diesel fuel applications.

In a preferred embodiment, the method of the present invention can be used to produce mesitylene and isopentane fuel from a biomass. The pathway to produce the mesitylene isopentane fuel is shown is FIG. 1. The acetone feed is produced from a biomass (not shown).

Acetone 1 recycled acetone 3 are pumped into reactor 5 to form mesitylene and mesityl oxide.

The catalyst employed in reactor No. 5 is preferably prepared according to the procedure described hereinafter.

Catalyst Synthesis

Impregnation Solution Example

Dissolve 30.04 g of tantalum powder in 200 ml of 48% hydrofluoric acid. Neutralize with 525 ml of 28% ammonium hydroxide—add 450 ml of water. Continue adding ammonium hydroxide until pH reaches 7. Filter the resulting precipitate. Wash the filter cake three times to remove residual fluoride. Dissolve 126.07 g of oxalic acid in 1 liter of water. Add the filter cake to this solution with stifling and heating. Mix until a clear solution is obtained. Assay the solution via gravimetry or absorption spectroscopy to obtain the weight percent of tantalum.

Catalyst Impregnation

Dry the catalyst base at 200 C overnight. Weigh out an appropriate volume of catalyst and use the formula below to obtain the proper solution weight.

$$\left(\begin{array}{c}\text{Target Weight}\\ \text{in 200 mL}\end{array}\right) = \left(\begin{array}{c}\text{Target \# of}\\ \text{mols oxide on}\\ \text{final catalyst}\end{array}\right)\left(\begin{array}{c}\text{MW of}\\ \text{Oxide}\end{array}\right)\left(\begin{array}{c}\text{Gravimetric}\\ \text{factor in oxide}\end{array}\right)\left(\frac{1}{\begin{array}{c}\text{fraction of metal in}\\ \text{salt solution by weight}\end{array}}\right)$$

Soak the catalyst base with the impregnating solution for at least one hour—ensuring that the liquid level just covers the catalyst base.

Catalyst Drying

Dry the catalyst in a conventional oven at 140-180 C. Ensure that the catalyst is thoroughly dry prior to final firing.

Catalyst Calcination

Calcine the catalyst at the defined temperature (generally 300 C) for the defined time (generally 11 hours). When the catalyst has cooled sufficiently, seal into a can until needed.

Catalyst Composition

Group V element oxides are preferred. Minimum catalyst loading is preferred for cost benefits—optimal loading is preferably from 1.0 to 4.5% of the oxide dispersed on a high surface silica bead.

Catalyst Evaluation and Use 68.85 grams of calcined catalyst is loaded into a 0.875-in diameter by 7.0-in length reactor barrel. The reactor is heated under flowing argon until operation temperature is reached –300350 C is preferred, but the reaction will run from 250-400 C. The maintained preferred pressure is 120 psig but the reaction will run from 50 to 180 psig. Acetone feed is then started. The acetone may be pure, or contain 10 to 20% water (or other diluents) which maintain activity and reduces coking. The Liquid Hourly Space Velocity explored has been 0.001 to 8 hr-1 the preferred range being 5 to 8 hr-1 to optimize activity and selectivity of mesitylene to mesityl oxide.

Catalyst Results

A number of runs using a number of different catalysts were carried out in reactor number 5 to measure the activity of these catalysts. The load hourly space velocity, the calcining time, calcining temperature, weight % of catalyst on the catalyst substrate, as well as the loading and activity are also set forth in tables 5-6 for catalyst of vanadium, tantalum and niobium.

TABLE 5

| LHSV | Calc Time | Calc Temp | Weight % | Loading | Activity |
|---|---|---|---|---|---|
| VANADIUM on Perlkat 97/0 | | | | | |
| 4 | 15 | 400 | 9.73 | 1401 | 1513 |
| 4 | 22 | 400 | 7.26 | 898 | 1361 |
| 3 | 11 | 600 | 1.77 | 232 | 1803 |
| 3 | 22 | 600 | 1.77 | 232 | 1929 |
| 3 | 11 | 300 | 2.79 | 363 | 1320 |
| 2 | 22 | 300 | 2.79 | 363 | 911 |

TABLE 6

| LHSV | Calc Time | Calc Temp | Weight % | Loading | Activity |
|---|---|---|---|---|---|
| NIOBIUM on Perlkat 97/0 | | | | | |
| 6 | 15 | 400 | 2.45 | 495 | 5839 |
| 4 | 11 | 400 | 4.72 | 611 | 3377 |
| 5 | 22 | 400 | 4.72 | 611 | 3860 |
| 4 | 11 | 600 | 3.85 | 498 | 2294 |
| 8 | 22 | 600 | 3.85 | 498 | 4831 |
| 8 | 11 | 800 | 3.23 | 420 | 2473 |
| 8 | 22 | 800 | 3.23 | 420 | 2866 |
| 6 | 11 | 300 | 4.98 | 648 | 5096 |
| 8 | 22 | 300 | 4.98 | 648 | 5943 |
| 7 | 11 | 500 | 4.17 | 542 | 4048 |
| 8 | 22 | 500 | 4.17 | 542 | 3998 |
| 8 | 15 | 300 | 0.96 | 125 | 5040 |
| 8 | 15 | 300 | 1.66 | 215 | 5315 |
| 8 | 15 | 300 | 3.04 | 395 | 6718 |
| 8 | 15 | 300 | 4.34 | 564 | 5419 |
| 8 | 15 | 300 | 5.75 | 745 | 5317 |
| 8 | 15 | 300 | 7.06 | 918 | 5477 |
| NIOBIUM on alumina | | | | | |
| 8 | 15 | 300 | 1.38 | 395 | 5045 |
| 8 | 15 | 300 | 1.22 | 395 | 7825 |

TABLE 7

| LHSV | Calc Time | Calc Temp | Weight % | Loading | Activity |
|---|---|---|---|---|---|
| TANTALUM on Perlkat 97/0 | | | | | |
| 6 | 15 | 400 | 7.36 | 957 | 3994 |
| 6 | 28 | 400 | 7.36 | 957 | 4885 |
| 8 | 11 | 400 | 7.60 | 988 | 6545 |
| 7 | 11 | 400 | 7.60 | 988 | 6181 |
| 8 | 22 | 400 | 7.60 | 988 | 6386 |
| 6 | 11 | 600 | 6.74 | 876 | 4573 |
| 8 | 22 | 600 | 6.74 | 876 | 5114 |
| 8 | 11 | 300 | 2.51 | 994 | 6537 |
| 8 | 22 | 300 | 2.51 | 994 | 7148 |
| 8 | 15 | 300 | 1.42 | 185 | 7776 |
| 8 | 15 | 300 | 2.75 | 342 | 7650 |
| 8 | 15 | 300 | 3.92 | 510 | 7758 |
| 8 | 15 | 300 | 5.16 | 670 | 7404 |
| 8 | 15 | 300 | 6.81 | 885 | 7366 |
| 8 | 15 | 300 | 0.84 | 110 | 6733 |
| 8 | 15 | 300 | 3.51 | 457 | 7217 |
| 8 | 15 | 300 | 4.40 | 572 | 6822 |
| 8 | 15 | 300 | 2.51 | 327 | 7364 |
| TANTALUM on alumina | | | | | |
| 8 | 15 | | 2.04 | 342 | 5387 |
| 8 | 15 | | 0.93 | 213 | 5432 |
| TANTALUM on Perlkat 79/3 | | | | | |
| 8 | 15 | | 2.03 | 342 | 9126 |
| 8 | 15 | | 1.02 | 171 | 7039 |
| TANTALUM on Perlkat 46/10 | | | | | |
| 8 | 15 | | 2.02 | 342 | 6211 |
| 8 | 15 | | 1.01 | 171 | 6434 |
| TANTALUM on silicia | | | | | |
| 8 | 15 | | 2.03 | 342 | 4738 |
| 8 | 15 | | 1.00 | 171 | 3922 |

Figure 11:
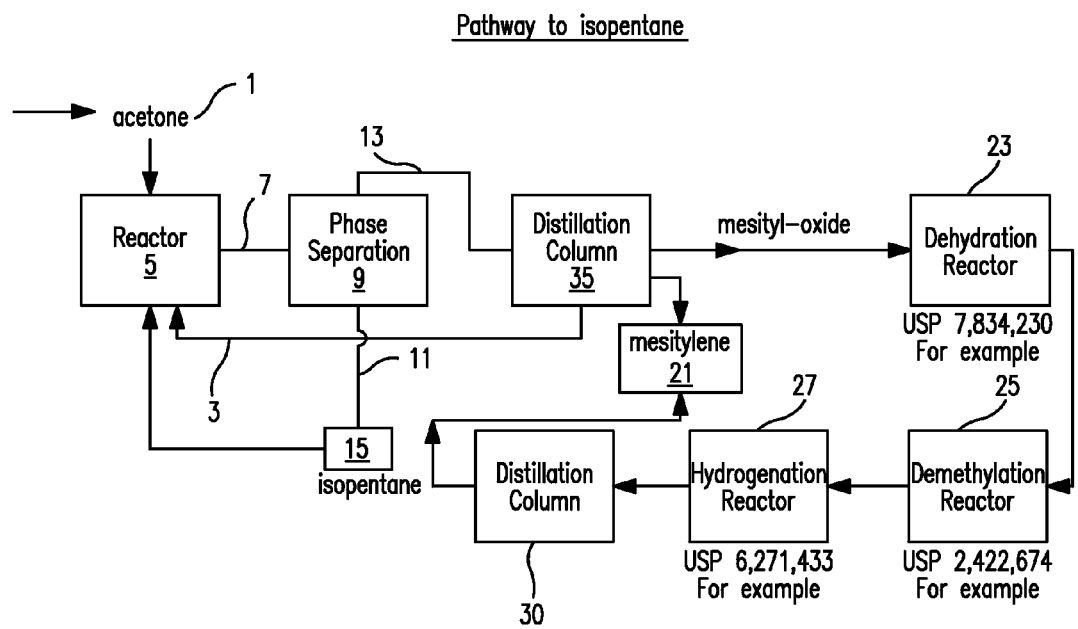
FIG. 11 is a block diagram of the method of the present invention, illustrating the path way employed in a preferred method of producing mesitylene-isopentane fuel.

As illustrated in FIG. 11, liquid effluent 7 from reactor 5 is than fed into phase separator 9, where it is separated into 2 phases, an aqueous phase 11 and an organic phase 13. The aqueous layer is then stripped in a distillation column 15 of the remaining unreacted acetone that is fed back into the previous reactor 5. The organic phase 13 is passed to a distillation column 35 where the mesitylene, mesityl oxide and other value chemicals are recovered.

Mesitylene is then passed to holding tank 21 for later fuel mixing. The mesityl oxide is sent to dehydration reactor 23, then to the demethylation reactor 25, and finally to hydrogenation reactor 27 to form isopentane. These three reactors 23, 25, and 27 carry out conventional processes. An example of a dehydration reactor is described in U.S. Pat. No. 7,834,230. An example of a demethylation reactor is described in U.S. Pat. No. 2,422,674, an example of a hydrogenation reactor 27 is described in U.S. Pat. No. 6,271,433. These three reactors 23, 25 and 27 may be separate or combined. The output of these reactors is then fed into a distillation column 30 to isolate Isopentane subsequent for mixing with mesitylene in tank 21.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. Method of producing a mesitylene-isopentane fuel, comprising:
    (a) in a gas phase reaction passing acetone in contact with a catalyst at a temperature of from about 250° C. to 400° C., at a liquid hourly space velocity of from about 1 to 8, and at a pressure of from about 50 to 200 psi, said catalyst comprising from about 0.5 to 10 wt % of one or more metal oxides selected from the group consisting of vanadium oxide, niobium oxide, and tantalum oxide obtained from water soluble salts thereof, whereby to form reaction products in which a portion of the acetone feed is trimerized to form mesitylene, and the remainder of acetone feed is either dimerized to form mesityl oxide or other by-products;
    (b) separating the mesitylene from other reaction products;
    (c) converting said mesityl oxide in a series of reactions to isopentane by subjecting the mesityl oxide of step (a) to dehydration, demethylation, and hydrogenation; and
    (d) mixing the separated mesitylene from step (b) with the isopentane obtained from step (c).

2. The method of claim 1, wherein acetone contacts the catalyst at a temperature of from about 275° C. to 375° C., at a liquid hourly space velocity of from about 2 to 8, and at a pressure of from about 75 to 175 psi.

3. The method of claim 1, wherein the catalyst comprises from about 0.5 to 7.0 wt % of metal oxide.

4. The method of claim 1, wherein the water soluble salts comprise one or more of vanadium oxalate, niobium oxalate, and tantalum oxalate.

5. The method of claim 1, wherein the metal oxides are impregnated on an acidic silicon-based substrate, and then the impregnated substrate is calcined at a temperature of from about 250° C. to 350° C. for a period of from about 11 to 22 hours.

6. The method of claim 1, wherein said mesityl oxide in step (c) is subjected to a dehydration reaction to form as reaction products methyl isopropenyl acetylene and 4-methyl-1,2,4 pentatriene.

7. The method of claim 6, wherein reaction products from the dehydration reaction are subjected to a demethylation reaction to form as reaction products of isopropenyl acetylene and/or 1,2,4 pentatriene.

8. The method of claim 7, wherein the isopropenyl acetylene and/or 1,2,4 pentatriene are all subjected to hydrogenation to form isopentane.

9. The method of claim 1, wherein the acetone is derived from (a) fermenting a biomass to produce a mixture of metabolites comprising acetone and butanol; and (b) separating the acetone from butanol and any ethanol or other solvents in the mixture by fractional distillation.

10. The method of claim 6, wherein the acetone is derived from: (a) fermenting a biomass to produce a mixture of metabolites comprising acetone and butanol; and (b) acetone from butanol and any ethanol or other solvents in the mixture by fractional distillation.

11. The method of claim 7, wherein the acetone is derived from: (a) fermenting a biomass to produce a mixture of metabolites comprising acetone and butanol; and (b) separating the acetone from butanol and any ethanol or other solvents in the mixture by fractional distillation.

12. The method of claim 8, wherein the acetone is derived from: (a) fermenting a biomass to produce a mixture of metabolites comprising acetone and butanol; and (b) separating the acetone from butanol and any ethanol or other solvents in the mixture by fractional distillation.

13. The method of claim 1, wherein the reaction products from step (a) are first subjected to a phase separation and then a fractional distillation to separate resultant mesitylene from other reaction products.

14. The method of claim 1, wherein step (a) results in a liquid effluent which is fed into a phase separator where it is separated into two phases, an aqueous phase and an organic phase.

15. The method of claim 14, wherein the aqueous layer is then stripped of any remaining unreacted acetone, that is fed back into the reaction in step (a) above.

16. The method of claim 15, wherein the organic phase is fed into a distillation column where mesitylene oxide and other by-products are recovered.

17. Method of producing a mesitylene-isopentane fuel, comprising: (a) in a gas phase reaction passing acetone in contact with a catalyst at a temperature of from about 250° C. to 400° C. and the liquid hourly space velocity of from about 1 to 8, and at a pressure of from about 50 to 200 psi, said catalyst comprising from about 0.5 to 10 wt % of one or more metal oxides selected from the group consisting of vanadium oxide, niobium oxide, and tantalum oxide obtained from water soluble salts thereof, whereby to form reaction products in which a portion of the acetone feed is trimerized to form mesitylene, and the remainder of acetone feed is either dimerized to form mesityl oxide or other by-products; (b) feeding liquid effluent from the reaction in step (a) above into a phase separator where it is separated into two phases, an aqueous and an organic phase; (c) stripping the aqueous layer of any remaining unreacted acetone, that is fed back into the reaction in step (a) above; (d) passing the organic phase into a distillation column where mesitylene, mesityl oxide and other by-products are recovered; (e) passing recovered mesitylene from step (d) to a holding tank; (f) converting said mesityl oxide in a series of reactions to isopentane by subjecting the mesityl oxide of step (a) to dehydration, demethylation, and hydrogenation; and (g) mixing the separated mesitylene from step (e) with the isopentane obtained from step (f).

18. The method of claim 17, wherein said mesityl oxide in step (f) is subjected to a dehydration reaction to form as reaction products methyl isopropenyl acetylene and 4-methyl-1,2,4 pentatriene.

19. The method of claim 18, wherein said methyl isopropenyl acetylene and 4-methyl-1,2,4 pentatriene are subjected to a demethylation reaction to form as reaction products isopropenyl acetylene and/or 1,2,4 pentatriene.

20. The method of claim 19, wherein reaction products from the isopropenyl acetylene and/or 1,2,4, pentatriene are subjected to hydrogenation to form isopentane.

21. A method of producing mesitylene, comprising:
(a) in a gas phase reaction passing acetone in contact with a catalyst
at a temperature of from about 250 to 400° C.,
at a liquid hourly space velocity of from about 1 to 8, and
at a pressure of from about 50 to 200 psi,
said catalyst comprising from about 0.5 to 10 wt % of one or more metal oxides selected from the group consisting of vanadium oxide, niobium oxide, and tantalum oxide, said gas phase reaction resulting in reaction products in which a portion of the acetone is trimerized to form mesitylene; and
(b) separating the mesitylene from other reaction products.

22. The method of claim 21, wherein acetone contacts the catalyst at a temperature of from about 275 to 375° C., at a liquid hourly space velocity of from about 2 to 8, and at a pressure of from about 75 to 175 psi.

23. The method of claim 21, wherein the catalyst comprises from about 0.5 to 7.0 wt % of metal oxide.

24. The method of claim 21, wherein the vanadium oxide, niobium oxide or tantalum oxide is obtained from a water soluble salt thereof.

25. The method of claim 24, wherein the water soluble salt comprises one or more of vanadium oxalate, niobium oxalate, and tantalum oxalate.

26. The method of claim 21, wherein the acetone is derived from (a) fermenting a biomass to produce a mixture of metabolites comprising acetone and butanol; and (b) separating the acetone from butanol and any ethanol or other solvents in the mixture by fractional distillation.

27. The method of claim 21, wherein step (b) comprises subjecting the reaction products from step (a) first to a phase separation and then to a fractional distillation to separate resultant mesitylene from other reaction products.

28. The method of claim 21, wherein step (a) results in a liquid effluent containing the reaction products, the liquid effluent being fed into a phase separator where it is separated into two phases, an aqueous phase and an organic phase.

29. The method of claim 28, wherein the aqueous phase is stripped of any remaining unreacted acetone, the stripped acetone being fed back into the step (a) reaction.

30. A method of producing a fuel comprising mesitylene and isopentane, comprising:
(a) in a gas phase reaction passing acetone in contact with a catalyst
at a temperature of from about 250 to 400° C.,
at a liquid hourly space velocity of from about 1 to 8, and
at a pressure of from about 50 to 200 psi,
said catalyst comprising from about 0.5 to 10 wt % of one or more metal oxides selected from the group consisting of vanadium oxide, niobium oxide, and tantalum oxide, said gas phase reaction resulting in reaction products in which a portion of the acetone is trimerized to form mesitylene;
(b) separating the mesitylene from other reaction products; and
(c) combining the mesitylene with isopentane.

31. The method of claim 30, wherein acetone contacts the catalyst at a temperature of from about 275 to 375° C., at a liquid hourly space velocity of from about 2 to 8, and at a pressure of from about 75 to 175 psi.

32. The method of claim 30, wherein the catalyst comprises from about 0.5 to 7.0 wt % of metal oxide.

33. The method of claim 30, wherein step (b) comprises subjecting the reaction products from step (a) first to a phase separation and then to a fractional distillation to separate resultant mesitylene from other reaction products.

34. The method of claim 30, wherein step (a) results in a liquid effluent containing the reaction products, the liquid effluent being fed into a phase separator where it is separated into two phases, an aqueous phase and an organic phase.

35. The method of claim 34, wherein the aqueous phase is stripped of any remaining unreacted acetone, the stripped acetone being fed back into the step (a) reaction.

\* \* \* \* \*